United States Patent
Lerner

(10) Patent No.: US 6,490,480 B1
(45) Date of Patent: Dec. 3, 2002

(54) APPARATUS AND METHODS FOR MEASURING AUTONOMIC NERVOUS SYSTEM FUNCTION

(76) Inventor: Eduard Lerner, A.J. Ernststraat 171, 1083 GT Amsterdam (NL)

(*) Notice: Subject to any disclaimer, the term of this patent is extended or adjusted under 35 U.S.C. 154(b) by 3 days.

(21) Appl. No.: 09/661,353

(22) Filed: Sep. 14, 2000

Related U.S. Application Data

(60) Provisional application No. 60/154,383, filed on Sep. 16, 1999.

(51) Int. Cl.[7] .................................................. A61B 5/05

(52) U.S. Cl. ........................................ 600/547; 600/587

(58) Field of Search ................................ 600/345–360, 600/373–384, 386 J, 508–528, 544–547, 587–595

(56) References Cited

U.S. PATENT DOCUMENTS 5,782,874 A * 7/1998 Loos .............................. 607/2

* cited by examiner

Primary Examiner—Michael Peffley
Assistant Examiner—Pamela Lynn Wingood
(74) Attorney, Agent, or Firm—Nixon & Vanderhye P.C.

(57) ABSTRACT

An apparatus and a non-invasive polygraphic diagnostic method electroautonomography are described. The invented apparatus can be used for diagnostic test to determine the function of the autonomic nervous system (ANS) of major organ systems. Further more, the invented apparatus and related test methods are used for measurement of the two types of skin potentials i.e. slow waves and fast waves. Since the fast waves displays possible clinical indications of autonomic nerve conduction velocity and other ANS function, the present apparatus and the non-invasive polygraphic method can be used for an early and accurate diagnostic tests for many diseases related to autonomic dysfunction and microneurography.

13 Claims, 5 Drawing Sheets

Three different types of skin potentials

Slow waves
(1 wave per
1-30 minutes)

30 minutes

Normal waves
(2-20 waves
per minute)

2 minutes

Fast waves
(2-15 waves
per second)

2 seconds

Healthy Subject

Multiple System Atrophy (MSA)

Measurement of EAG, EGG and ECG baseline

APPARATUS AND METHODS FOR MEASURING AUTONOMIC NERVOUS SYSTEM FUNCTION

I claim priority from my provisional application No. 60/154,383, filed Sep. 16, 1999.

BACKGROUND OF THE INVENTION

Field of the invention

The invention relates to an apparatus and non-invasive methods to assess autonomic nervous system (ANS) function. By simultaneous recording of electrophysiological and other physiological signals, a complete indication of ANS function can be obtained in just one diagnostic test instead of numerous separate tests.

The autonomic nervous system (ANS) is concerned with the regulation of smooth muscle, cardiac muscle and every other visceral organ in the body. The autonomic nervous system is not directly accessible to voluntary control. Instead, it operates in an automatic fashion on the basis of autonomic reflexes and central control. One of its major functions is the maintenance of homeostasis within the body. The ANS further plays an adaptive role in the interaction of the organism with its surroundings. The ANS has two functionally and anatomically distinct divisions: the sympathetic part and the parasympathetic part.

In many diseases the sympathetic and the parasympathetic parts of the ANS are affected leading to autonomic dysfunction. The evaluation of the presence of ANS disorders requires in interpretation of numerous laboratory tests like blood pressure measurements, heart-rate and respiration-rate recordings, evaluation of the endocrine system and tilt table tests etc. In our prior U.S. Pat. No. 5522386 we disclose a new polygraphical method called electroautonomography (EAG), which can be used to determine the central and/or peripheral ANS function including the autonomic innervation and control of major organ systems as well as of local ANS function. The method is based on the polygraphical recording of skin potentials or electrodermal activity and is called electrovegetography. The electrovegetograph as described in our previous art is based on a sensitive (AC or DC) amplifier means specifically capable of registering skin potentials. Generally skin potentials are recorded with an AC amplifier in combination with the filter settings within the following band pass 0.1–40 Hz. A typical skin potential registration contains skin potential frequencies approximately between 0.033 and 0.33 Hz and amplitudes that can range between 0.05–2.0 mV. These values are based on rest recordings before the occurrence of habituation. The initial high amplitudes are thought to be a result of the subject's emotional status. After several minutes the amplitudes decrease to a level that reflect ANS activity. Upon stimulation the amplitude of the skin potentials may raise up to 5 mV. The extent of the reaction to the stimulus is thought to be largely depended on the subject's ANS activity.

The determination of the so called autonomic nerve conduction velocity or NCV can be more accurately performed using the fast waves obtained from skin potential recordings, because these fast waves display a sharp onset of an evoked response, whereas the "normal skin potentials" do not always display a sharp onset and especially not after the occurrence of habituation. This characteristic of "normal" skin potentials complicates the calculation of the autonomic nerve conduction velocity, resulting in wrong calculations of the NCV. In practice this may mean for instance that a beginning neuropathy is not detected, whereas the calculation of the NCV using the fast waves is much less susceptible for mistakes even after the occurrence of habituation, and will therefore facilitate the early diagnosis of neuropathy and other disorders that affect the autonomic nerve fibers. The fast waves can also be used to detect a neuropathy in any part of the mammalian body.

The fast waves can be further used in an alternative microneurographic measurement method. Microneurography or intraneural recording is an invasive technique, which is used to assess sympathetic activity. For such a measurement a needle microelectrode is inserted directly into a nerve.

It is therefore an object of this invention to use a non-invasive method to measure fast waves of the skin potentials and any other electrophysiological signals.

It is also an object of this invention to determine autonomic conduction velocity presented by fast wave recordings to evaluate the autonomic nerve system's function.

It is further object of this invention to provide an early and accurate diagnostic test for many diseases of autonomic dysfunction.

SUMMARY OF THE INVENTION

The objects set forth above as well as further and other objects and advantages of the present invention are achieved by the embodiments of the invention described hereinbelow.

The present invention relates to an apparatus and methods to measure any type of electrophysiological signals and especially the measurement of skin potentials characterized by low frequency oscillations and high frequency oscillations. These types of skin potentials are called slow waves and fast waves respectively. As "normal" skin potentials the slow waves and fast waves are suggested to be generated by and to be under control of the ANS.

The slow waves can be detected preferably with a DC amplifier means. The "normal" skin potentials are superimposed on the slow waves. The slow waves can be detected preferably with the high pass filter switched off and the low pass filter set at 0.01 Hz. The observed wavelengths with these filter settings may range between 24 hours and 2 minutes, whereas the amplitudes may vary between 100_V and 5 mV in rest recordings. The amplitude may change with values up to 25 mV upon stimulation. We suggest that these slow waves reflect cycles in metabolism and ANS and most likely sympathetic activity.

The fast waves can be measured with a sensitive DC amplifier means, but are more preferably measured with a sensitive AC amplifier means. In order to detect the fast waves, the band pass of the filters need to be set at 0.1–40 Hz, preferably the band pass is set at 0.5–30 Hz and more preferably the band pass is set at 1–10 Hz, The frequencies of the observed fast waves may range between 2–15 Hz, but frequencies higher than 15 Hz do also exist. The amplitudes of the fast waves may range between 2 and 200_V. These fast waves are generated by and under the control of ANS activity, particularly by parasympathetic activity. The fast waves are not only present in the spectrum of skin potentials, but they can be present in any electrophysiological signal that is recorded superficially or with a needle electrode inserted in any organ or tissue of a mammal's body. The slow and fast waves possibly reflect the tone of the ANS.

The following analysis method may be used in a preferred embodiment for the fast waves, and the existing signal:

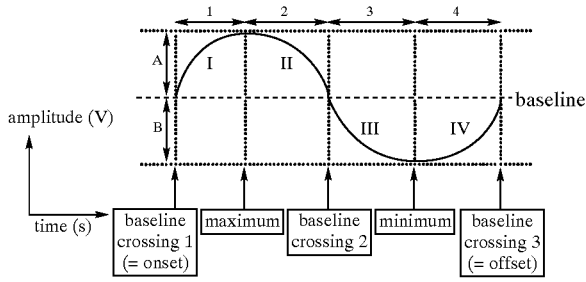

The letters refer to amplitudes in either _V or mV at the maximum respectively and minimum, whereas the figures refer to the time periods in either milliseconds or seconds. The Roman figures refer to the area under the curve of each of the four segments. Now we will call the quotient: [A/1] the negative reactivity index and the quotient: [A/2] the negative recovery index of the wave. The quotients [B/3] and [B/4] will be the curve's positive reactivity and positive recovery indices respectively. We further suggest to define the time segments 1+2 as _a; the time, segments 3+4 as the whole period (1+2+3+4) as _, which is a commonly used symbol for the wavelength.

From a selected portion of the measured values, all the described parameters are averaged and for each index (negative and positive reactivity, negative and positive recovery, _a, _b, _and area) its relative occurrence in a selected part of the measured values is calculated. Healthy organisms will have indices within a certain range whereas organisms with a dysfunctional ANS will have indices that deviate from the indices range of healthy ones.

In addition to the measurement of skin potentials, the apparatus is further adapted to measure any other in practice known electrophysiological signal like but not limited to the electrocardiogram, the electro-encephalogram, the electrogastrogram, and the electro-oculogram. Further, the apparatus is equipped with means to measure any in practice known physiological signal like, but not limited to: blood-pressure, oxygen saturation, plethysmography, and respiration.

The present invention relates to the simultaneous measurement of a variety of electrophysiological parameters but not limited to: the electrovegetogram extended with the analysis of fast and slow waves, the electrocardiogram (heart rate and heart rate variability), the electrogastrogram (gastric rate, variability of the gastric rate and variability of the amplitude). Optionally as part of the EAG measurement, the evaluation of fast and/or slow, waves of electrophysiological signals other than the skin potentials may be included. In addition to parameters obtained from electrophysiological signals, also minimal one parameter from physiological measurements is being evaluated. The physiological parameter being chosen from, but is not limited to the following group: respiration rate and variability in respiration rate and respiration amplitude, blood pressure variability, oxygen saturation variability, variability in plethysmogram. The influence of sensory stimuli chosen from and not limited to the following group: sound, electric, magnetism, vibration, olfaction, taste, light and pressure on the measured electro- and non- electrophysiological signals are evaluated as well. The results obtained from an EAG recording with and without the application of sensory stimuli to the organism under investigation i.e. a human being or any other mammal will provide the investigator in just one test with information about the status of the ANS of his patient. The information includes the following: the autonomic control of the cardiac and blood vessels functioning, obtained from the blood pressure and/or saturation measurements as well as from evaluation of the heart rate variability in rest and during the application of external stimuli as those generated by stimuli generator and internal stimuli generated by for instance the Valsalva maneuver, deep breathing, stop breathing and mental stress. The autonomic functioning of the stomach is obtained from the evaluation of the electrogastrogram. The analysis of the respiration frequency and variability of respiration frequency and amplitude in rest and during stimuli provide the investigator with information about the central regulation of the lung function, central and/or peripheral ANS functioning is determined with the analysis of the simultaneous skin potential recording from both hands and feet. Due to the integration of many parameters in one test, the disclosed diagnostic method will therefore be an welcome alternative to the existing methods, which are based on separate standard tests that are used for the diagnosis of ANS related disorders.

The apparatus comprises separate AC and DC amplifier modules or AC/DC amplifier modules, whereof the AC and DC amplifier modules have a minimum sensitivity of 72 nV. The AC/DC amplifier recorders are constructed to minimize electric interference between the separate AC and the DC amplifier modules. The amplifier modules are constructed to minimize cross interference between the modules. The underlying reason for the use of separate modules is to minimize the amount of noise coming from the amplifier module and/or from the external environment. This noise may obscure relevant information of the measured signal, which in turn may complicate the interpretation and analysis of the measured signal. The highest acceptable noise is 2_Vpp when electrodes are connected to the input The disclosed apparatus can be (when preferred) extended with additional amplifier modules. For example, an apparatus comprising of four AC amplifier modules may be supplemented with for instance six AC/DC amplifier modules.

Optionally, the apparatus is equipped to detect and warn the operator for extra noise sources and bad connections prior to and during operation of the apparatus.

According to the invention, the apparatus comprises at least one amplifier module. Preferably the apparatus comprises of at least 8 amplifier modules and most preferably the apparatus comprises of at least 16 amplifier modules.

The disclosed apparatus comprises of at least one auxiliary input means for measurement of non-electrophysiological signals. Preferably the apparatus comprises of at least four auxiliary input means and most preferably it comprises of at least six auxiliary input means.

The apparatus according to the present invention comprises a stimulus generator. The stimulus generator is adapted to produce one or more external stimuli chosen from but not limited to following group: sound, electricity, magnetism, light, pressure, olfaction, taste, and vibration. The generator is adapted to produce adjustable stimuli strengths and sequences and the generator is further adapted to be operated manually as well as automatically. The generator means being fully isolated from the amplifier modules to prevent signal distortion and to maintain a low noise level.

In the present invention, the apparatus is associated with a computer means for data acquisition, data processing and control. Further the computer means controls the set up of the apparatus and comprises software filters for the signals coming from the amplifier modules. In a preferred embodiment the computer means is fully integrated with the disclosed apparatus.

The measured values may be processed by any suitable analyzing techniques known in practice such as, but not limited to: the above described method for the analysis of fast waves and skin potentials, wave-form analysis, statistical analysis, correlation techniques, fast Fourier, and Fourier analysis.

The measured values may be subject to any mathematical operation and the result of a mathematical operation being visible. For example, the software of the disclosed apparatus is adapted to subtract the skin potential signal and the EGG signal from the ECG and is adapted to display the result of these subtractions.

Additionally in selected parts of the measured signal, the relative occurrence (in percentage) of any other parameter of interest may be calculated. For example, the amplitude at each maximum in selected parts of the measured signal is the parameter of interest now, the occurrence of the same amplitude value in the selected parts is presented in percentage.

Other objects, features and advantages will be apparent from the following detailed description of preferred embodiments taken in conjunction with the accompanying drawings in which:

BRIEF DESCRIPTION OF THE DRAWINGS

With respect to FIG. 3, the upper four channels are the skin potentials from both hands and feet, the fifth channel shows an electrogastrogram, the sixth channel shows an electrocardiogram and the seventh channel gives a respiration signal obtained with a respiration belt. The electroautonomogram of the healthy subject shows a synchrony between the skin potentials from the four extremities. The electroautonomogram of the MSA patient is completely different from that of a healthy person. In this electroautonomogram there is a synchrony between the signals of the hands and the signals from the feet but not between hands and feet. The uncoupling of the signals indicate a central ANS dysfunction.

DETAILED DESCRIPTION OF THE PREFERRED EMBODIMENTS

EXAMPLE 1

Figure 1:
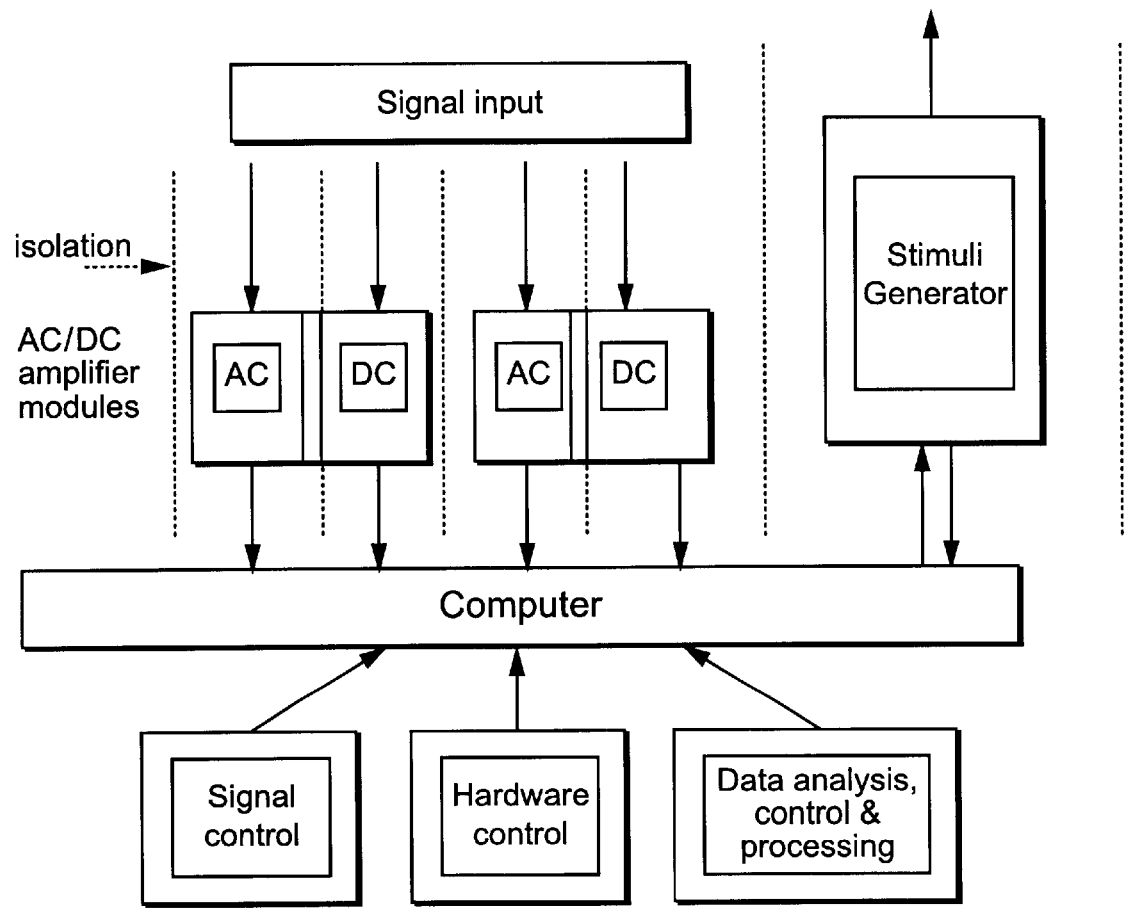
FIG. 1 gives a schematic view of the electroautonomograph with two AC/DC amplifier modules. The EAG can however comprise of one and any other number of AC/DC modules, or one or any other number of modules comprising of just AC or just DC amplifier means or any combination thereof.
Figure 2A:
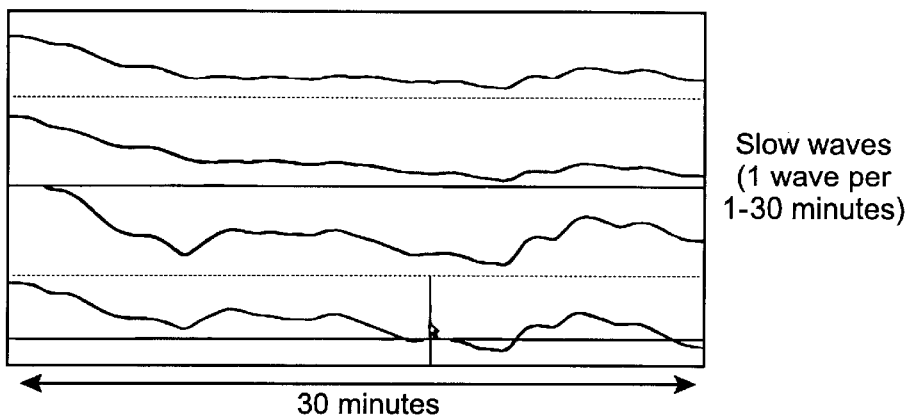
FIG. 2A shows a recording of the slow waves of three different types of skin potentials.
Figure 2B:
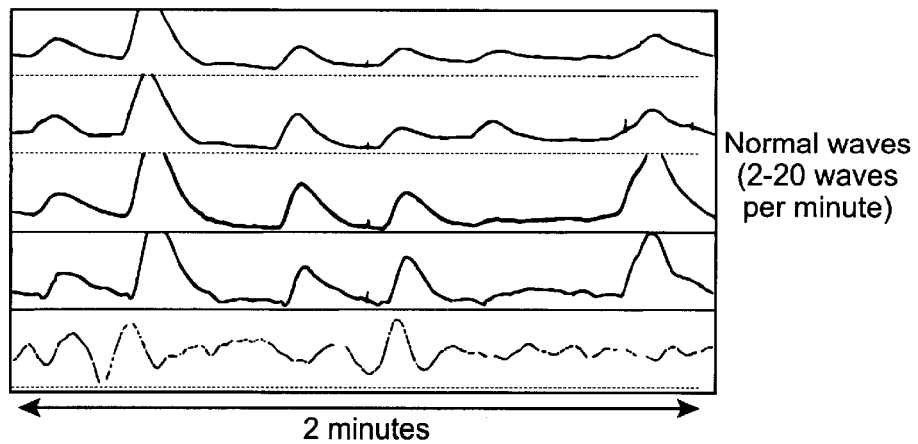
FIG. 2B shows normal skin potentials for these three skin types.
Figure 2C:
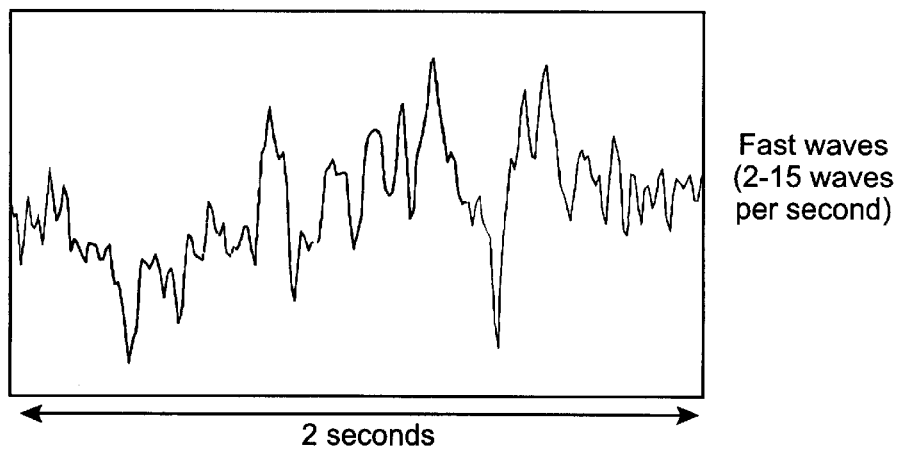
FIG. 2C shows the fast waves.
Figure 3A:
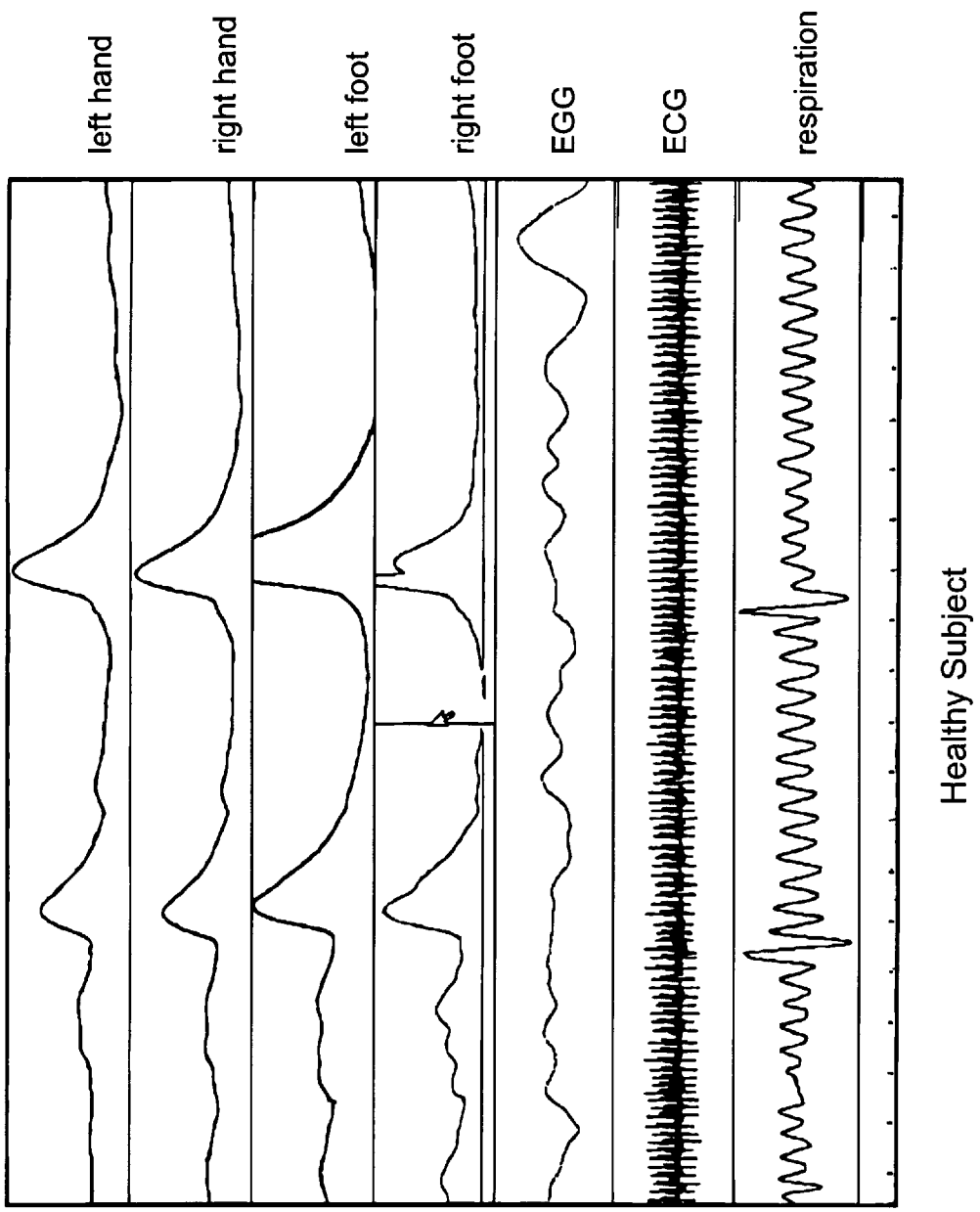
FIG. 3A shows an electroautonomogram of a healthy subject.
Figure 3B:
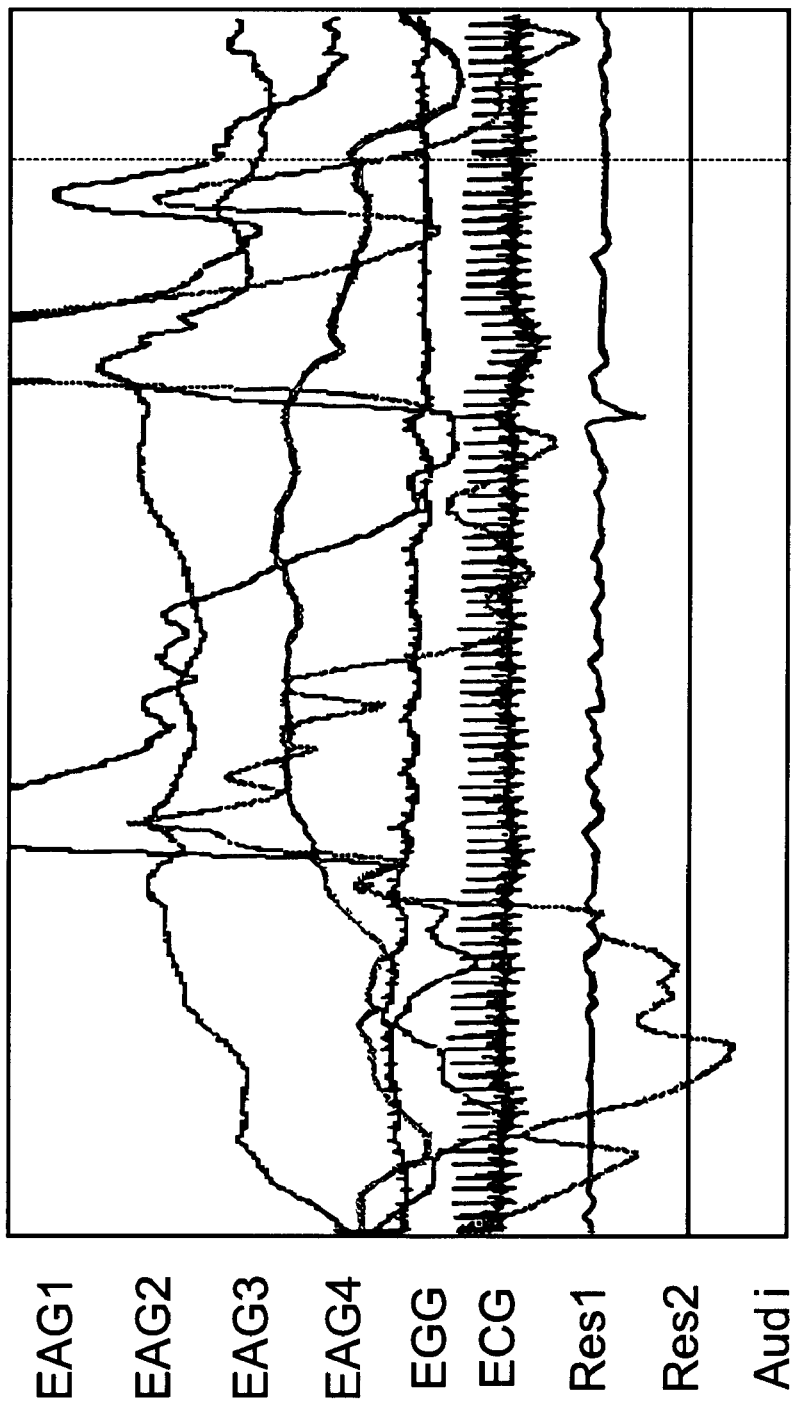
FIG. 3B shows an electroautonomogram of a patient diagnosed with Multiple System Atrophy (MSA)
Figure 4A:
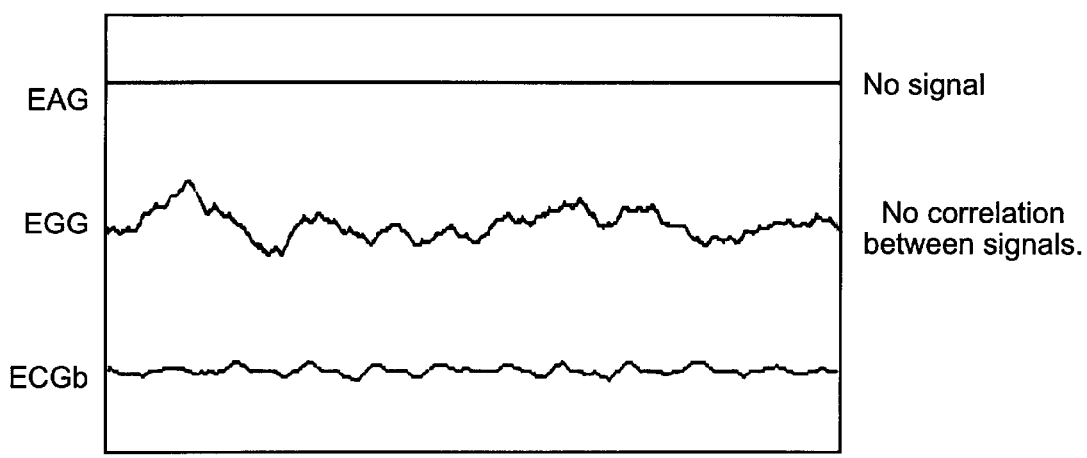
FIG. 4A shows the different phases in slope of the measurement of EAG, EGG and ECG baseline when there is no correlation between the EAG, EGG and ECG baseline (ECGb)
Figure 4B:
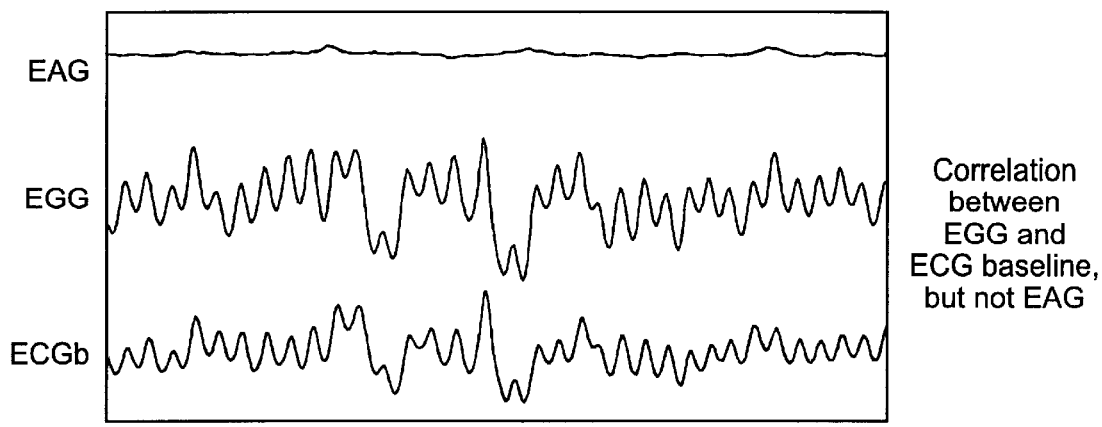
FIG. 4B shows a correlation between the EGG and ECGb but not with the EAG.
Figure 4C:
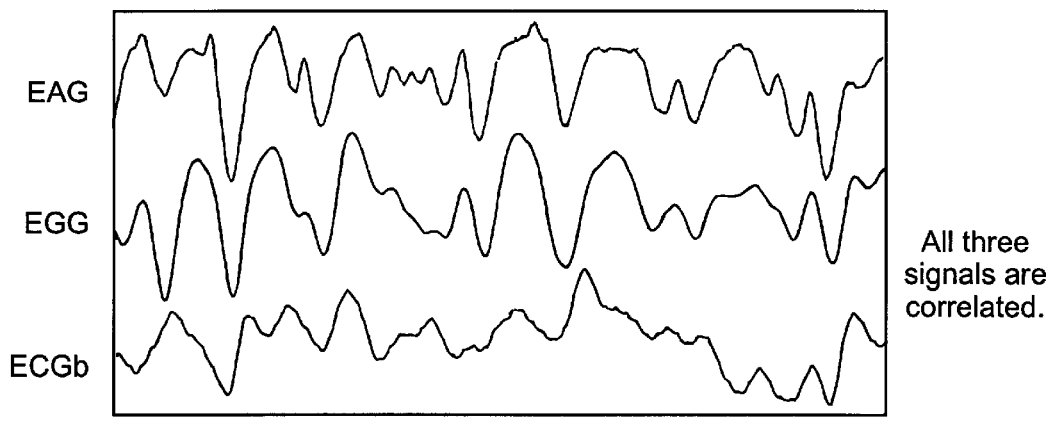
FIG. 4C shows all three signals are correlated.

In a preferred embodiment the fast waves can be recorded with an AC or DC amplifier means. The high pass filter is set at 0.5 Hz. preferably the high pass filter is set at 0.7 Hz and more preferably the high pass filter is set at 1.0 Hz. The low pass filter is set at 2000 Hz, preferably the low pass filter is set at 40 Hz, and more preferably the low pass filter is set at 10 Hz. Surface electrode (s) for this fast waves measurement can be placed at any reachable site on the body i.e. skin and mucosa epithelium from the eyes, nose, mouth, vagina or rectum. A non-invasive microneurographic recording can thus be made from one or more places at the same time. Like the existing invasive microneurographic methods the present non-invasive variant provides information about ANS activity. The amplitudes of the fast waves are about 20 times lower than the potentials recorded direct (invasively) from a single fiber, due to signal dampening by the skin. The observed frequencies are however completely comparable: a microneurogram comprises of signals within 2–15 Hz and these frequencies are also observed in a fast waves recording with the above mentioned filter settings.

EXAMPLE 2

This example describes a possible embodiment of electroautonomography. An organism i.e. a human being or an animal under investigation is in a preferably supine position. Active electrodes for skin potential(including the slow and fast waves) measurement are fixed on the palmar and plantar sites of both hands and feet, respectively, whereas the passive electrodes are fixed on the back surface of the hands and feet or any other less electro-active point. The electrocardiogram, ECG is recorded preferably from the chest and the electrogastrogram, EGG, is recorded from the superficial projection of the stomach on the abdomen or on the back or a combination thereof. A respiration measurement is performed by means that measure the nose flow or by means of a respiration belt or by any other in practice known means to measure the respiration. Additionally to respiration the blood pressure can be measured. The blood pressure measurement is preferably performed with means that are capable to register a continuous signal with a minimum occurrence of device generated stimuli, that interfere with the measurement of the other parameters. An example of a suitable blood pressure device is the Finapress®. Further in addition to respiration measurement and/or blood-pressure measurement, the saturationcan be measured. The saturation is preferably measured with a device which is capable to register the oxygen saturation continuously without generating external or internal stimuli to the subject. The simultaneous measurement of all these different parameters with and without stimulation provides the investigating physician with information of the ANS functioning.

In another embodiment of the invention, electroautonomography or EAG can be used together with a tilt table test. As an alternative to the tilt table test, the following method may be used: an organism i.e. a human being or any other mammal under investigation is in a supine position and an EAG recording as described above is being performed. During the second part of the measurement the investigated subject is still in a supine position, but with one or two of his extremities raised, or even with all four extremities raised. The capability of the heart and blood vessels to compensate for the change in blood volume is thus measured. Because the autonomic nervous system plays an important role in the regulation of the heart and the blood vessels, a possible dysfunction will be detected by EAG, A possible practical application of this embodiment is the testing for orthostatic disorders e.g. orthostatic intolerance.

In a yet other embodiment of the invention, electroautonomography can be used as a tool to investigate sleep and to determine the role of the ANS in sleeping disorders. During sleep, periods of signal synchronization among the ECG base line, the EGG and the skin potentials were observed.

EXAMPLE 3

In a typical sleep EAG recording, measurements were made of the EEG (electro-encephalogran) bilaterally from the frontal to the occipital area, the EOG (electrooculogram), ECG, the skin potentials from one hand, the EGG and the respiration. At the beginning of sleep, the amplitudes of the skin potentials and the gastric potentials are low. The heart is in this stage correlated with the respiration signal. In a later phase of sleep the gastric waves raise in amplitude and there can also a raise in the amplitudes of the skin potentials be observed. The baseline of the heart changed in appearance and there may be little or no correlation left between the baseline and the respiration signal. At the onset of REM sleep, characterized by the EOG and the EEG signals, all electrophysiological signals changed rapidly in amplitude, but mostly they decreased also rapidly to a slightly higher level than their previous values. However, there can be remarkable correlation observed between the EGG. ECG baseline and the skin potentials. The correlation can occur between all three of these signal between just either two of them. The occurrence of periods of highly synchronized signals may continue until the end of the sleep. Because the ANS is for instance involved in the regulation and control of the heart, stomach and the generation of skin potentials, we suggest on basis of the results obtained from our sleeping studies that the ANS has an integrative function during sleep. The involvement of the ANS in sleeping disorders can be easily detected by abnormalities in the electroautonomogram such as for instance the absence of synchronization. EAG is thus also a diagnostic method to investigate sleeping disorders.

It is concluded from the sleeping studies that the ECG signal is contaminated with signals derived from the skin and from the stomach. The computer software of the disclosed apparatus is adapted to distract a skin potential signal and the EGG signal from the ECG, resulting in a cleaner ECG signal. The resulting ECG can be used to detect early abnormalities in cardiac; function and eventually abnormalities that currently cannot be detected due to the noise in the ECG.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Method for measuring electrophysiological signals in aid of analyzing autonomic nervous system (ANS) function of a mammal comprising the steps of:

(a) imposing two waves of varying electrical signals upon the mammal's neurological system—a relatively slow wave and a relatively fast wave, utilizing one or more neurological system pathways for transit by such waves, (b) recording or displaying fast wave and slow, signals (c) making frequency comparisons of each of such wave signals as affected by interaction with the neurological system of the test subject and the combinations of such wave signals as affected by interaction with the neurological system of the test subject to respective baselines, whereby an enhanced sensitivity of measurement of ANS function is achieved to effect a fast wave-slow wave measurement.

2. The method of claim 1 wherein the baseline is response of the subject at a different time.

3. The method of claim 1 wherein the baseline is response of the subject under changed conditions such as exercise, changed body orientation or stimulus.

4. The method of claim 1 wherein the baseline is response of another subject or other calibration baseline external to the subject.

5. The method of claim 1 wherein the fast wave-slow wave ANS measurement is an electroautonomographic method.

6. The method of claim 5 wherein the said fast wave-slow wave measurement is made in combination with one or more other physiological measurements of mammal functions affected by or affecting ANS functions and the fast wave-slow wave measurements are correlated with the other measurements.

7. The method of claim 6 wherein the other measurement is selected from the group consisting of blood pressure, respiration measurement, saturation measurement, electrocardiogram, electroencephelogram, electrogastrogram and electrooculogram.

8. The method of claim 1 wherein the fast wave-slow wave measurement is made in multiple parallel channels.

9. The method of claim 1 wherein the fast wave-slow wave measurement is applied to skin potential ANS measurement.

10. Apparatus for practicing the method of claim 1 comprising means for establishing a varying fast wave and slow wave signal through one or more neurological pathways of a mammal's autonomic nervous system (ANS) subject with at least an order of magnitude (power of ten) differential of frequency between fast and slow waves and means for displaying and/or recording the waves.

11. Apparatus according to claim 10 comprising frequency filters to establish the waves and parallel AC and DC amplifiers for measurement.

12. Apparatus of claim 10 comprising means for making multi-channel fast wave-slow wave ANS function measurements.

13. Apparatus of claim 10 comprising means for effecting at least one additional measurement in combination with the fast wave-slow wave measurement and correlating results of the multiple measurements.

* * * * *